(12) United States Patent
Thiruvengadam et al.

(10) Patent No.: US 11,475,564 B2
(45) Date of Patent: Oct. 18, 2022

(54) NON-INVASIVE NON-CONTACT SYSTEM AND METHOD FOR MEASURING HEALTH PARAMETERS

(71) Applicant: AARCA RESEARCH INC., Orange, CT (US)

(72) Inventors: Jayanthi Thiruvengadam, Tamil Nadu (IN); Gayathri Choda, Andhra Pradesh (IN)

(73) Assignee: AARCA RESEARCH INC., Orange, CT (US)

( * ) Notice: Subject to any disclaimer, the term of this patent is extended or adjusted under 35 U.S.C. 154(b) by 134 days.

(21) Appl. No.: 17/014,040

(22) Filed: Sep. 8, 2020

(65) Prior Publication Data

US 2021/0073983 A1 Mar. 11, 2021

(51) Int. Cl.
*A61B 5/00* (2006.01)
*A61B 5/01* (2006.01)
(Continued)

(52) U.S. Cl.
CPC .......... *G06T 7/0012* (2013.01); *A61B 5/0077* (2013.01); *A61B 5/015* (2013.01);
(Continued)

(58) Field of Classification Search
CPC ......... G06T 7/0012; G06T 2207/10016; G06T 2207/10032; G06T 2207/30104; G06T 2207/30201; A61B 5/0077; A61B 5/015; A61B 5/02055; A61B 5/6803; A61B 5/02438; A61B 5/0816; A61B 5/4866; A61B 2576/00; H04N 5/33
(Continued)

(56) References Cited

U.S. PATENT DOCUMENTS

2016/0180050 A1* 6/2016 Holmes .................. G16H 10/65
705/3
2017/0224257 A1* 8/2017 Rogers ................ A61B 5/0537
(Continued)

FOREIGN PATENT DOCUMENTS

CN 109428917 A * 3/2019
JP 2011067371 A * 4/2011
(Continued)

*Primary Examiner* — Albert Kir
(74) *Attorney, Agent, or Firm* — Gearhart Law LLC; David Postolski, Esq.

(57) ABSTRACT

A system and method for measuring health parameters of a subject is disclosed. The system and method are based on a mirror; an image acquisition unit configured with the mirror, and comprising a thermal sensor for capturing thermal images or videos of a body part of the subject; and a processing unit to receive data packets associated with the captured thermal images or videos from the image acquisition unit to identify a region of interest of the body part in each frame of the captured thermal images and videos. Further, the processing unit extracts attributes associated with a heat intensity variation from the identified region of interest region, and compares the extracted attributes with a predetermined set of reference data to measure risk scores associated with the health parameters of the subject based on the comparison. The measured risk scores are displayed by a display unit.

16 Claims, 3 Drawing Sheets

(51) Int. Cl.
  *A61B 5/024* (2006.01)
  *G06T 7/00* (2017.01)
  *H04N 5/33* (2006.01)
  *A61B 5/0205* (2006.01)
  *A61B 5/08* (2006.01)
(52) U.S. Cl.
  CPC ........ *A61B 5/02055* (2013.01); *A61B 5/6803* (2013.01); *H04N 5/33* (2013.01); *A61B 5/02438* (2013.01); *A61B 5/0816* (2013.01); *A61B 5/4866* (2013.01); *A61B 2576/00* (2013.01); *G06T 2207/10016* (2013.01); *G06T 2207/10032* (2013.01); *G06T 2207/30104* (2013.01); *G06T 2207/30201* (2013.01)
(58) Field of Classification Search
  USPC .......................................................... 348/77
  See application file for complete search history.

(56) References Cited

U.S. PATENT DOCUMENTS

| | | | | |
|---|---|---|---|---|
| 2019/0150763 | A1* | 5/2019 | Gladshtein | A61B 5/02007 |
| 2019/0167211 | A1* | 6/2019 | Everman | A61B 5/0205 |
| 2021/0153752 | A1* | 5/2021 | Park | A61B 5/746 |

FOREIGN PATENT DOCUMENTS

| | | | |
|---|---|---|---|
| KR | 20160056338 A | * | 5/2016 |
| WO | WO-2020011719 A1 | * | 1/2020 |

\* cited by examiner

— NON-INVASIVE NON-CONTACT SYSTEM AND METHOD FOR MEASURING HEALTH PARAMETERS

This application claims priority to Indian Application No. 201941035980, filed Sep. 6, 2019. The disclosure of which is incorporated herein by reference.

TECHNICAL FIELD

The present disclosure relates to health care systems for monitoring the health condition of persons. More particularly, the present disclosure relates to a system and method for measuring health parameters of persons.

BACKGROUND

The background description includes information that may be useful in understanding the present invention. It is not an admission that any of the information provided herein is prior art or relevant to the presently claimed invention, or that any publication specifically or implicitly referenced is prior art.

A daily health check is essential for people who are suffering from chronic diseases like cardiovascular disease (CVD), diabetes, hypertension and lipidemia. In a medical centre, a trained medical personnel performs these tests. In recent days, in-home environment handheld devices are also used to monitor these conditions. Each of these conditions require a different device which involve traditional invasive techniques like drawing blood samples from a finger prick of an individual, causing pain and discomfort. This invasive procedure demotivates people to avoid regular health checks, and a healthy person does not put efforts to do these checks causing delay in detection of the condition.

There is no efficient and common existing device/system that may collectively monitor the cardiovascular disease, cerebrovascular disease, diabetes, hypertension, thyroid monitoring and lipidemia. Devices that are available only for the specific disease, and may require the subject/person/individual to visit a physician or trained operator to perform tests and/or collect data related to the condition of the diseases. The diseases like diabetes require the subject to visit a physician daily or to use the invasive technique at home to record the blood sugar levels. The existing devices for monitoring diabetes involve invasive techniques where the subject has to take blood samples by pricking, and the samples are analyzed for observing the blood glucose values. The hypertension is diagnosed based on pressure values observed for a week or two. The cardiovascular complications require the subject to visit a physician for monitoring heart rate using devices like Electrocardiography (ECG) machines. This requires fixing of electrodes on the patient's body leading to discomfort. The lipidemia monitoring is again invasive, where blood samples are to be analyzed causing discomfort and delay in getting results.

There is, therefore, a need in the art to provide a simple and efficient non-invasive non-contact system and method for real-time monitoring health parameters of an individual

OBJECTS OF THE INVENTION

A general object of the present disclosure is to provide a simple and efficient solution which may obviate the foregoing limitations of conventional devices.

An object of the present disclosure is to provide an improved system and method for measuring and/or monitoring health parameters of an individual.

Another object of the present disclosure is to provide a common system that may collectively monitor various diseases like cardiovascular disease, cerebrovascular disease, diabetes, hypertension, thyroid monitoring, lipidemia etc. of a subject, such as humans.

Still another object of the present disclosure is to provide a simple and cost-effective health parameters measurement system and method which uses techniques, which are, robust, accurate, efficient, cost-effective, and easy to implement.

SUMMARY

Aspects of the present disclosure relate to health care systems for monitoring health conditions of individuals. More particularly, the present disclosure relates to a system and method for measuring health parameters of individuals. The system may collectively monitor various diseases like cardiovascular disease, cerebrovascular disease, diabetes, hypertension, thyroid monitoring, lipidemia etc.

In an aspect, the present disclosure provides a system and method for measuring one or more health parameters of a subject, such as humans. The proposed system and method are based on a set of glasses comprising at least one glass, a frame for holding the set of glasses, and an image acquisition unit configured with the set of glasses. At least one glass may be a two way mirror. The image acquisition unit may include a thermal sensor for capturing any or a combination of one or more thermal images and videos of at least one body part, for example a face of the subject. The image acquisition unit may include an optical camera to capture any or a combination of one or more optical images and videos of the at least one body part of the subject. A processing unit that is operatively coupled to the image acquisition unit, and may be configured to identify a region of interest of the body part in each frame of the captured any or a combination of the one or more thermal images and videos. Identification of the region of interest may be based on correlation of the captured thermal images and/or videos with the captured optical images and/videos. The processing unit may extract one or more attributes associated with a heat intensity variation from the identified region of interest region in each frame of the captured thermal images and/or videos for comparing the extracted attributes with a predetermined set of reference data that are stored in a database operatively coupled to the processing unit to measure risk scores associated with one or more health parameters of the subject. The one or more health parameters may be selected from a group comprising a metabolic rate, state of diabetes mellitus condition, state of hypertension, state of dyslipidemia, body temperature, heart-rate, respiratory rate, and the like. Thus, it would be appreciated that the risk scores associated with one or more health parameters of the subject are determined non-invasively without contacting the subject and does not involve any harmful radiation. Hence, various diseases like cardiovascular disease, cerebrovascular disease, diabetes mellitus, hypertension, hyperthyroidism or hypothyroidism, dyslipidemia etc. of the subject may be monitored in real-time non-invasively without touching the subject.

In an embodiment, the system may include a display unit to display measured risk scores associated with the one or more health parameters. The display unit may be configured with at least one glass, and operatively coupled to the processing unit. The display unit may include a user interface to receive inputs from users.

Various objects, features, aspects and advantages of the inventive subject matter will become apparent from the following detailed description of preferred embodiments, along with the accompanying drawing figures in which like numerals represent like components.

BRIEF DESCRIPTION OF THE DRAWINGS

In the figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

DETAILED DESCRIPTION

Figure 1A:
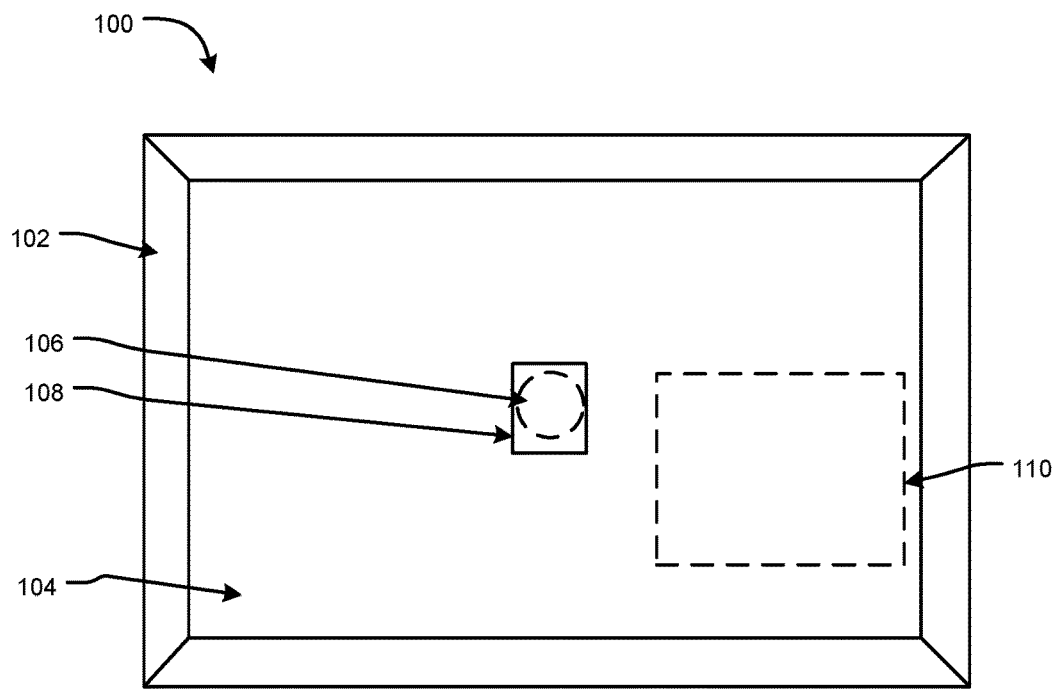
FIGS. 1A and 1B illustrate exemplary front view and rear view of a schematic diagram of the proposed system for measuring health parameters of a subject, in accordance with an embodiment of the present disclosure.

The following is a detailed description of embodiments of the disclosure depicted in the accompanying drawings. The embodiments are in such detail as to communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Various methods described herein may be practiced by combining one or more machine-readable storage media containing the code according to the present invention with appropriate standard computer hardware to execute the code contained therein. An apparatus for practicing various embodiments of the present invention may involve one or more computers (or one or more processors within a single computer) and storage systems containing or having network access to computer program(s) coded in accordance with various methods described herein, and the method steps of the invention could be accomplished by modules, routines, subroutines, or subparts of a computer program product.

While embodiments of the present invention have been illustrated and described, it will be clear that the invention is not limited to these embodiments only. Numerous modifications, changes, variations, substitutions, and equivalents will be apparent to those skilled in the art, without departing from the spirit and scope of the invention, as described in the claim.

Embodiments explained herein relates to health care systems for monitoring health conditions of individuals. More particularly, the present disclosure relates to a system and method for measuring, in real-time, health parameters of individuals.

Mirror, a standard appliance in every household, and this may be used to facilitate monitoring of health parameters of individuals using non-invasive techniques, thus it may facilitate passive monitoring. Though, there are earlier versions of smart medical mirrors, they are designed as a display device or another screen to show existing information. Moreover, the other 'medical mirrors' which use a standard digital camera measure a pulse rate or a heart rate only. In the existing devices, the pulse rate is the physiological data that is displayed on a screen. The pulse rate is calculated using video from a standard digital light camera. The other physiological data if any displayed is either collected from mobile applications or collected from wearable devices on the subject.

According to an aspect, the present disclosure provides a system and method for real-time monitoring of health parameters of a person. This is a hardware setup for monitoring and diagnosing vascular healthiness or health parameters of the subject.

In an aspect, the present disclosure provides a system and method for measuring one or more health parameters of a subject, such as humans. The proposed system and method are based on capturing one or more thermal images and videos of at least one body part, for example face, of the subject using a thermal sensor, such as thermal camera, of an image acquisition unit configured with a set of glasses comprising at least one glass, and/or capturing any or a combination of one or more optical images and videos of the at least one body part of the subject through an optical camera of the image acquisition unit. Further, the captured thermal images and/or videos and/or the captured optical images and/or videos may be received by a processing unit to identify a region of interest of the body part in each frame of the captured thermal images and/or videos. Identification of the region of interest of the body part may be based on correlation of the captured thermal images and/or videos with the optical images and/videos. Further, the processing unit may extract one or more attributes associated with a heat intensity variation from the identified region of interest region in each frame of the captured thermal images and/or videos to compare the extracted attributes with a predetermined set of reference data that are stored in a database operatively coupled to the processing unit to measure risk scores associated with one or more health parameters of the subject. A display unit may be operatively coupled to the processing unit to display measured risk scores associated with one or more health parameters on the at least one glass. The health parameters may be selected from a group comprising a metabolic rate, state of diabetes mellitus condition, state of hypertension, state of dyslipidemia, body temperature, heart rate, respiratory rate, and the like. Thus, it would be appreciated that the risk scores associated with one or more health parameters of the subject are determined non-invasively without contacting the subject and does not involve any harmful radiation.

Figure 1B:
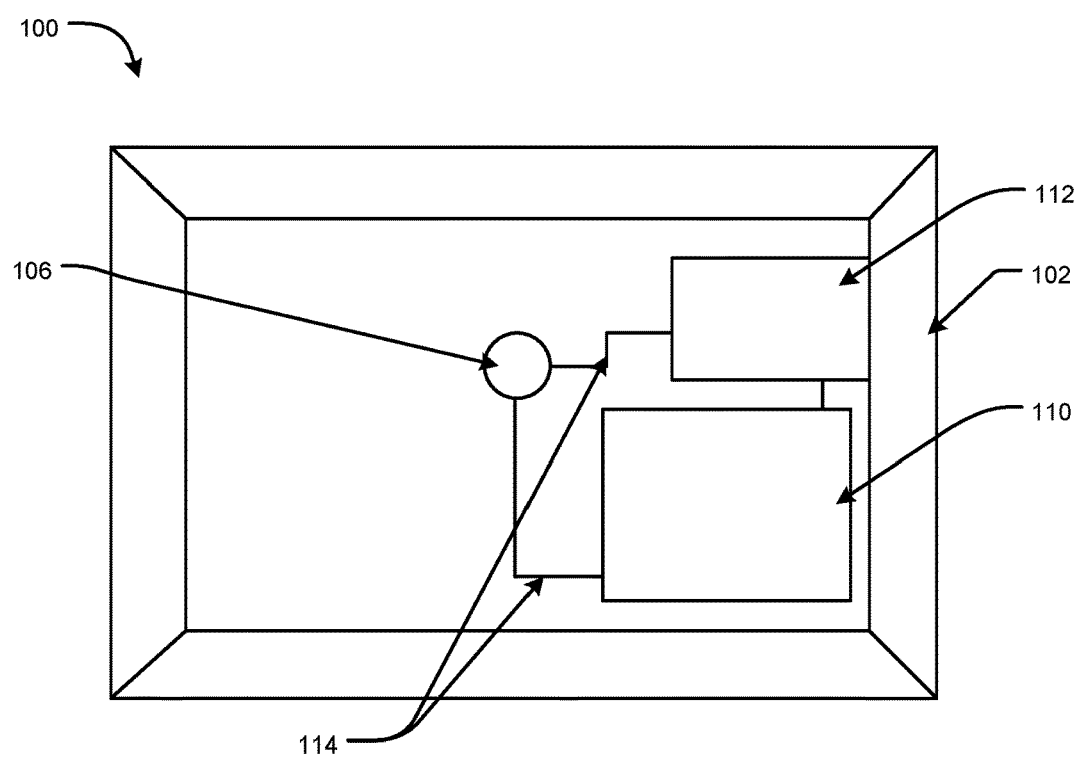

Referring to FIGS. 1A and 1B, where schematic diagrams of the proposed system are shown. In an embodiment, the proposed system 100 may include a frame 102, and a set of glasses that may include at least one glass 104 that is supported by the frame 102, and an image acquisition unit configured with the glass 104. The frame 102 may be made of any of wood, plastic, light weight metals, or any suitable material to suitably hold and support the mirrors and other elements of the system 100. In an embodiment, the glass 104 may be selected from a group comprising transparent glasses, translucent glasses, partially transparent glasses, and two-way mirrors. In a preferred embodiment, the glass 104 may be a two-way mirror.

In an embodiment, the image acquisition unit may include a thermal sensor 106, such as a thermal camera or infrared camera for capturing any or a combination of one or more thermal images and videos of at least one body part, such as face, of a subject, for example human. The thermal sensor 106 may sense heat or infrared radiation emitted from the body part of the subject and renders images and videos representing a spatial intensity of radiation. The thermal sensor may be configured to capture the thermal images and/or videos when the body part is oriented at a first predefined angle with respect to the thermal sensor 106. The thermal sensor 106 may be positioned behind the glass 104. The thermal images/videos may be generated by capturing infrared radiations emitted by a surface of the body part of the subject. The emitting IR radiation is corresponding to the surface temperature of the body part.

In another embodiment, the image acquisition unit may include an optical camera (not shown) to capture any or a combination of one or more optical images and videos of the at least one body part of the subject. The optical camera may be configured for identification of the body part of the subject. The optical camera may be configured to capture the optical images and/or videos when the body part of the subject is oriented at a second predefined angle with respect to the optical camera. In an embodiment, the optical camera may be positioned at any suitable position with the mirror 102 to capture the optical images/videos. In an embodiment, the optical camera may be placed behind the glass 104 adjacent to the thermal sensor 106 to capture the face of the subject. The optical images/videos may be generated by capturing light that reflects on the surface of the body part of the subject.

In an embodiment, the first predefined angle and second predefined angle may be same or different, based on an orientation of the subject in front of the glass 104.

In another embodiment, the image acquisition unit may further include a scanner unit (not shown) for scanning the at least one body part of the subject or full body of the subject. The scanner unit may be configured for authentication, identification and determining an orientation of the subject. In an embodiment, the scanner unit may be positioned at any suitable position with the mirror 102 to smay the subject. The scanner unit may be placed behind the glass 104, at upper portion top or at the center of the glass 104, and may be positioned at an angle to image the subject.

In an embodiment, the image acquisition unit may include an illuminating source (not shown) that may be used in conditions wherein the natural light is dull. The illuminating source may be configured such that it may provide a flash of light or a continuous light such that the one or more images may be captured with precision, accuracy, clarity and the like.

In an embodiment, the captured thermal images or the thermal video, or the optical images and the optical video may be stored on a first database. It would be appreciated that the first database may either be located locally on the image acquisition unit or the first database may be located on a cloud/server.

In an embodiment, a black vinyl wrap with one side adhesive film may be stuck on at least a portion of a rear side of the glass 104 such that the glass 104 acts as a mirror. The black vinyl wrap may be applied carefully to leave a space open, for example in the middle of the mirror, for exposing the thermal sensor 104, if the glass 104 is not permissible to infrared radiations.

In another embodiment, the glass 104 may include a slot to expose the thermal sensor 104, and a shutter 108 configured with the slot in the glass 104. The shutter may be configured for closing and opening the slot in the glass 104 to cover and uncover, respectively, the thermal sensor 106.

In an embodiment, if the glass 104 is made of material such as silicon or germanium where there is the possibility for infrared radiation to pass through the glass 104, then the slot in the glass 104 and the shutter 108 may not be required.

In an embodiment, the system 100 may include a display unit 110 configured with the glass 104, and operatively coupled with the image acquisition unit. The display unit 110 may include a display monitor. The display unit 110 may be configured with the glass 104 such that at least a portion, for example a left half of the system 100, acts as a mirror, and a right half may act as a display to display information.

In an embodiment, the display unit 110 may be positioned behind the glass 104 to display information on the glass 104. In another embodiment, the display unit 110 may be positioned beside the glass 104 in the right half of the system 100.

In an embodiment, the system 100 may include a processing unit 112 operatively coupled with the image acquisition unit and the display unit 110. The processing unit 112 may include one or more processors coupled to a memory. The memory may store a set of instructions executable by the one or more processors. The processing unit 112 may receive data packets associated with the captured thermal images and/or videos, and/or the captured optical images and/or videos, and scanned images from the image acquisition unit.

In an embodiment, the system 100 may include a transceiver or a communication unit (not shown) that is operatively coupled to the processing unit 112, and the image acquisition unit, and the display unit 110. The transceiver may be configured to wirelessly transmit information to other computing devices. The transceiver may include Wi-fi and/or Bluetooth units for data transmission and subsequent storage of data in any external storage device or the computing devices.

In an embodiment, the transceiver may include a voice recognizer to receive and/or recognize voice commands from users to control open/close of shutter, voice commands for capturing the thermal images/video by the thermal sensor and/or capturing optical images/videos by the optical camera, and/or for scanning the subject in front of the glass 104.

In an embodiment, the camera shutter 108 may be opened and closed using the voice control/command. In case of using the glass 104 of silicon or germanium glass, or any specific type of glass where infrared may pass through, the shutter 108 is not necessary. The black vinyl wrap may have hole to accommodate the thermal sensor 104. In an embodiment, black vinyl wrap may have holes to accommodate the optical camera and the scanner unit. Hence, the system architecture may include with or without the shutter 108. The shutter 108 may be made of any of a glass, plastic, metals, or any other suitable materials. In an embodiment, the shutter 108 may be actuated by a motor for covering and uncovering the thermal sensor 106.

In an exemplary embodiment, the processing unit 112 may be a Raspberry Pi or a similar device that can help with processing. At the rear side of the glass 104, the frame 102 may have a space/housing for attaching a power adapter, and/or a power source such as batteries to supply power to the image acquisition unit, display unit 110, processing unit 112 and other electronic components of the system 100.

In an exemplary embodiment, the image acquisition unit including the thermal sensor 104, optical camera and the scanner unit, and display unit 110 may be coupled to the processing unit 112 through wire cables 114.

In an embodiment, the processing unit 112 may be configured to identify a region of interest, for example forehead, of the body part of the subject in each frame of the captured thermal images and videos. The processing unit 112 may correlate the captured any or a combination of one or more thermal images and videos with the captured any or a combination of one or more optical images and videos to identify the region of interest.

In an exemplary embodiment, during correlation the processing unit 112 may acquire the captured one or more thermal images or thermal video, and the one or more optical images and optical video. Each of the captured one or more thermal images or each frame of the captured thermal video may be overlaid to the captured one or more optical images or each frame of the captured optical video to assist in defining the region of interest (ROI) for the captured thermal images or the captured thermal video.

In an embodiment, the processing unit 112 may be configured to extract one or more attributes associated with a heat intensity variation from the identified region of interest, for example forehead region, in each frame of the captured thermal images/videos to determine a blood flow, an artery region, and frequency properties of the blood flow in the artery region in the identified region of interest.

In an embodiment, the processing unit 112 may be configured to compare the extracted one or more attributes with a predetermined set of reference data. The reference data may be stored in a database, which may be a first database or a second database, operatively coupled to the processing unit. It would be appreciated that the second database may be located locally or on a cloud/server.

Based on the comparison, the processing unit 112 may measure risk scores associated with one or more health parameters of the subject. The health parameters are selected from a group comprising a metabolic rate, state of diabetes mellitus condition, state of hypertension, state of dyslipidemia, body temperature, heart rate, respiratory rate, and the like. The measured risk score of the subject may help to monitor the health parameters in real-time.

In an exemplary embodiment, the processing unit 112 may include a set of instructions/algorithms to identify the region of interest, such as the forehead, for feature extraction for measuring risk score.

In an embodiment, the display unit 110 may be configured to display the measured risk scores associated with the one or more health parameters. Further, the display unit 100 may include a user interface for interacting with users. In another embodiment, the display unit 10 may include a touch sensitive display or interface to receive inputs from the users, or displaying various options or interactive instructions to the users.

In another exemplary embodiment, the processing unit of the system may be implemented in any computing device that may be configured/operatively coupled with a server. The processing unit may be implemented using any or a combination of hardware components and software components such as a server, a computing system, a computing device, a security device and the like, such that embodiments of the present disclosure may determine the health condition of the subject/person. Further, the processing unit may be operatively coupled with the image acquisition unit through a network. Further, the image acquisition device may be integrated with imaging devices. The imaging devices may include, but not limited to, a digital camera, the thermal imaging camera, optical camera, a scanner, and a proximity sensor. The display unit 110 may be operatively coupled with the processing unit through the network.

The network may be a wireless network, a wired network or a combination thereof that may be implemented as one of the different types of networks, such as Intranet, Local Area Network (LAN), Wide Area Network (WAN), Internet, and the like. Further, the network may either be a dedicated network or a shared network. The shared network may represent an association of the different types of networks that may use a variety of protocols, for example, Hypertext Transfer Protocol (HTTP), Transmission Control Protocol/Internet Protocol (TCP/IP), Wireless Application Protocol (WAP), and the like.

Figure 2:
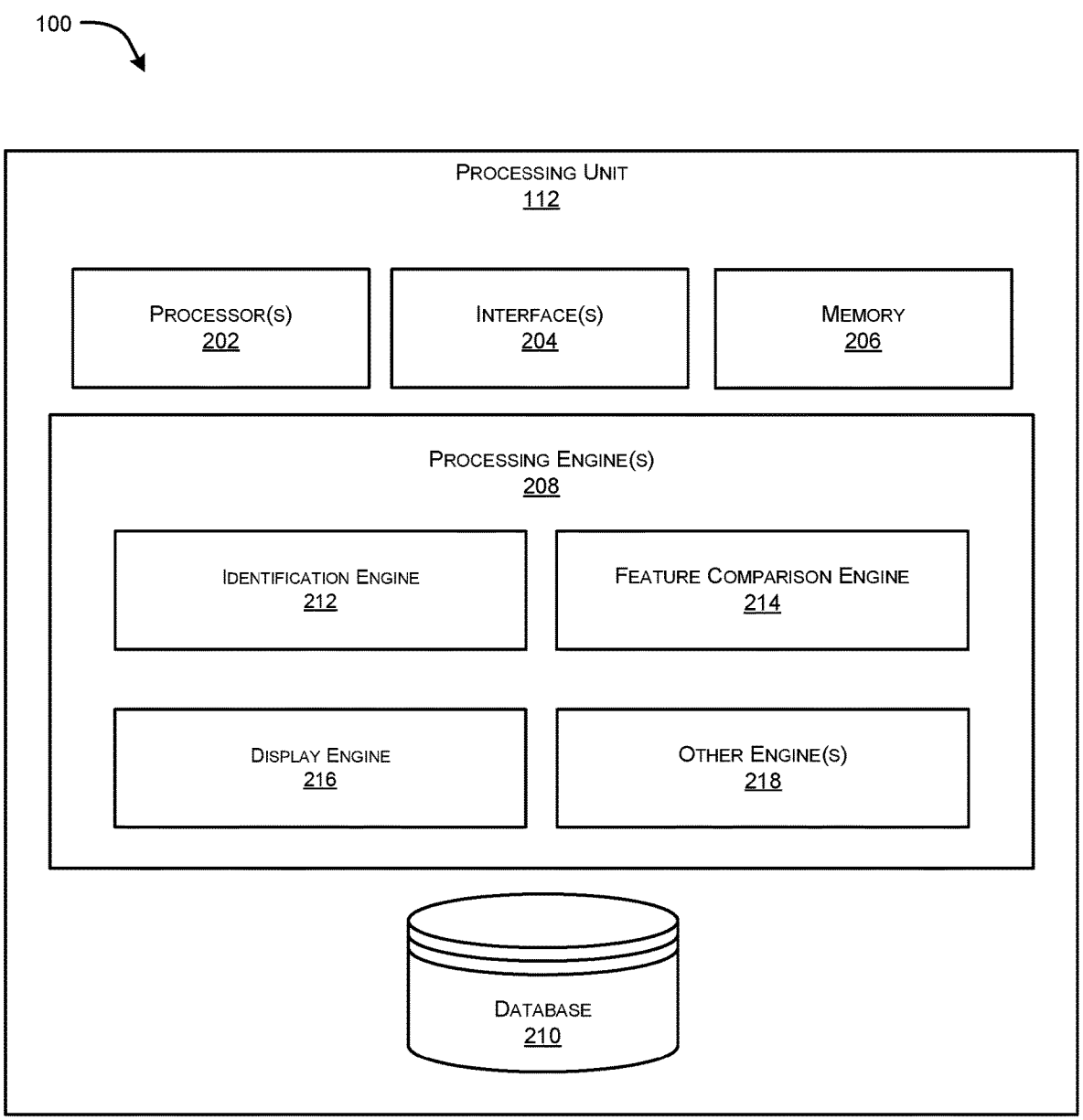
FIG. 2 illustrates exemplary functional components of the proposed system for measuring health parameters of a subject, in accordance with an embodiment of the present disclosure.

In an embodiment, the system 100 may facilitate real-time monitoring of the various health parameters, such as but not limited to, metabolic rate, state of diabetes mellitus condition, state of hypertension, state of dyslipidemia, body temperature, heart rate, respiratory rate, and the like. Further, the health parameters may be monitored non-invasively using the system 100. Thus, the system 100 may collectively or individually monitor various diseases like cardiovascular disease, cerebrovascular disease, diabetes, hypertension, thyroid monitoring, lipidemia etc. of the subject FIG. 2 illustrates exemplary functional components of the proposed system for measuring health parameters of a subject, in accordance with an embodiment of the present disclosure.

In an aspect, the system 100 may include a processing unit 112 that may include one or more processor(s) 202. The one or more processor(s) 202 may be implemented as one or more microprocessors, microcomputers, microcontrollers, digital signal processors, central processing units, logic circuitries, and/or any devices that manipulate data based on operational instructions. Among other capabilities, the one or more processor(s) 202 are configured to fetch and execute computer-readable instructions stored in a memory 206 of the processing unit 112. The memory 206 may store one or more computer-readable instructions or routines, which may be fetched and executed to create or share the data units over a network service. The memory 206 may comprise any non-transitory storage device including, for example, volatile memory such as RAM, or non-volatile memory such as EPROM, flash memory, and the like.

The processing unit 112 may also include an interface(s) 204. The interface(s) 204 may include a variety of interfaces, for example, interfaces for data input and output devices, referred to as I/O devices, storage devices, and the like. The interface(s) 204 may facilitate communication of processing unit with various devices coupled to the processing unit 112 such as the input unit and the output unit. The interface(s) 204 may also provide a communication pathway for one or more components of the processing unit 112. Examples of such components include, but are not limited to, processing engine(s) 208 and a database 210.

The processing engine(s) 208 may be implemented as a combination of hardware and programming (for example, programmable instructions) to implement one or more functionalities of the processing engine(s) 208. In examples described herein, such combinations of hardware and programming may be implemented in several different ways. For example, the programming for the processing engine(s) 208 208 may be processor-executable instructions stored on a non-transitory machine-readable storage medium and the hardware for the processing engine(s) 208 may comprise a processing resource (for example, one or more processors), to execute such instructions. In the present examples, the machine-readable storage medium may store instructions that, when executed by the processing resource, implement the processing engine(s) 208. In such examples, the processing unit 112 may comprise the machine-readable storage medium storing the instructions and the processing resource to execute the instructions, or the machine-readable storage medium may be separate but accessible to the processing unit and the processing resource. In other examples, the processing engine(s) 208 may be implemented by electronic circuitry.

The database 210 may include data that may be either stored or generated as a result of functionalities implemented by any of the components of the processing engine(s) 208. The database 210 may also include a first database, a second database, predefined reference data/parameters, and other required data, algorithms and instructions. The database 210 may be present locally or may be present on cloud/server.

In an exemplary embodiment, the processing engine(s) 208 may include an identification engine 212, a features comparison engine 214, a display engine 216 and other engine(s) 218.

It would be appreciated that modules being described are only exemplary modules, and any other module or sub-module may be included as part of the system. These modules too, may be merged or divided into super-modules or sub-modules as may be configured.

Identification Engine 212

In an aspect, the identification engine 212 may receive the captured one or more thermal images or thermal video, and/or one or more optical images and the optical video from the image acquisition unit of the system 100 as described in FIGS. 1A and 1B. The identification engine 212 may identify a region of interest (ROI), for example forehead, of the at least one body part, for example face, of the subject in each frame of the captured thermal images and video. Identification of the region of interest may be based on correlation of each of the one or more captured thermal images or thermal video with one or more optical images or the optical video to identify the region of interest. In an exemplary embodiment, during correlation each of the captured one or more thermal images or each frame of the captured thermal video may be overlaid to the captured one or more optical images or each frame of the captured optical video to assist in identifying the ROI for the captured thermal images or the captured thermal video. Those skilled in the art would appreciate that the thermal image may be captured using the thermal sensor such as a thermal camera, the thermal camera may sense thermal or infrared radiations emitted from the body part of the subject and may capture images representing the spatial intensity of radiation. The captured thermal images may have various thermal and/or infrared related features. The thermal and/or infrared related features may be very specific for the body part of the subject. Therefore, the ROI needs to be defined for the specific body part. Since, the thermal images are not very crisp and are not able to reveal clean, clear, distinct images of the body part.

In an embodiment, an optical imaging device such as an optical camera may be used for capturing the optical images of the body part captured by the thermal camera. In an embodiment, the identification engine 212 may assist in correlating or overlapping of the captured thermal images or the thermal video and the optical images or the optical video. Further, the ROI may be defined based on the body part that needs to be identified. The captured optical images may also be used for identification of the subject as the optical images provide very clean and clear images of the body part.

In an embodiment, the identified ROI may be resized to at least a first resolution image and a second resolution image. The first resolution image pertains to half of the resolution of the ROI and the second resolution image pertains to quarter of resolution of the ROI. It would be appreciated that the ROI portion of the image may be resized to half and a quarter of its total size to ensure faster processing of the image frames. The working of the resizing operation may be clear by considering an example, for example, an input image frame of dimensions (1280×960) is provided to the identification engine 212, the correlation engine 212 may consider an ROI of dimension (1280×336) containing all columns and upper rows from the input image frame.

Further, the identification engine may resize the ROI to the first resolution that may be a half-resolution, e.g. (640× 168) and the second resolution that may be a quarter of resolution, e.g. (320×84). The first resolution image and the second resolution image may then be utilized for further processing. Those skilled in the art would appreciate that the identification engine 212 focuses on enhancement and performs certain operations on the input image frames to ensure that processing in subsequent stages through the implementation of various other engines may be performed in less computational time.

Features Comparison Engine 214

According to an embodiment, the features comparison engine 214 may be configured to receive the thermal images with the identified ROI for each of the captured one or more thermal images or the captured thermal video. Now, based on the identified ROI one or more attributes may be extracted from the thermal images or videos by the feature comparison engine 214. The attributes may include, but not limited to, the heat intensity variation in the ROI to identify a blood flow, an artery region, frequency properties of the blood flow in the artery region.

Further, the extracted one or more attributes may be compared or matched with a predetermined set of reference data. The predetermined set of reference data may be stored in the database 210. The predetermined set of reference data may include a set of predefined threshold values pertaining to the extracted one or more attributes associated with the health parameters.

In response to the comparison of the at least one of the extracted one or more attributes with a predetermined set of reference data the processing unit 112 may be configured to determine/measure risk scores associated with one or more health parameters of the subject. The measured risk scores of the subject may help to monitor the health parameters in real-time. In an embodiment, the health parameters may be any or combinations of a metabolic rate, state of diabetes mellitus condition, state of hypertension, state of dyslipidemia, body temperature, heart rate, respiratory rate, and the like etc.

In an exemplary embodiment, a scanner unit of the system as described in FIGS. 1A and 1B may be configured to scan the body part, for example face, of the subject. The scanned face of the subject may be used for any or a combination of authentication, identification and checking the orientation of the face of the subject etc. In an embodiment, the scanned image may be a three-dimensional image of the face of the subject. The features comparison engine 214 may be configured to extract one or more facial features from the scanned image of the subject. Now, the extracted one or more facial features may be compared with a facial dataset.

The facial dataset may include a set of predefined threshold facial features associated with various faces of various subjects for authentication and/or identification or for determining the orientation of the face. The facial dataset may be stored in the database 210. The orientation of the face may be used for adjusting the first angle and the second angle, or adjusting the face of the subject.

Display Engine 216

According to an aspect, the display engine 216 may be configured to generate display signals. The generated display signals may be transmitted to the display unit 110. The generated display signals may include any or a combination of the risk scores of the health parameters, the identified subject, the authentication information etc. In an embodiment, the display engine 216 may help generate an interface on the display unit 216 to establish an interactive interface that may facilitate various interactions with users.

It would be appreciated by the person skilled in the art that the measured risk score of the health parameters may be easily monitored on the display unit 110. The display unit 110 may be a display associated with a computing device such as a mobile phone.

Further, the various data and the risk score of the health parameters being displayed may be stored in the display unit 110 and/or the database 210.

Figure 3:
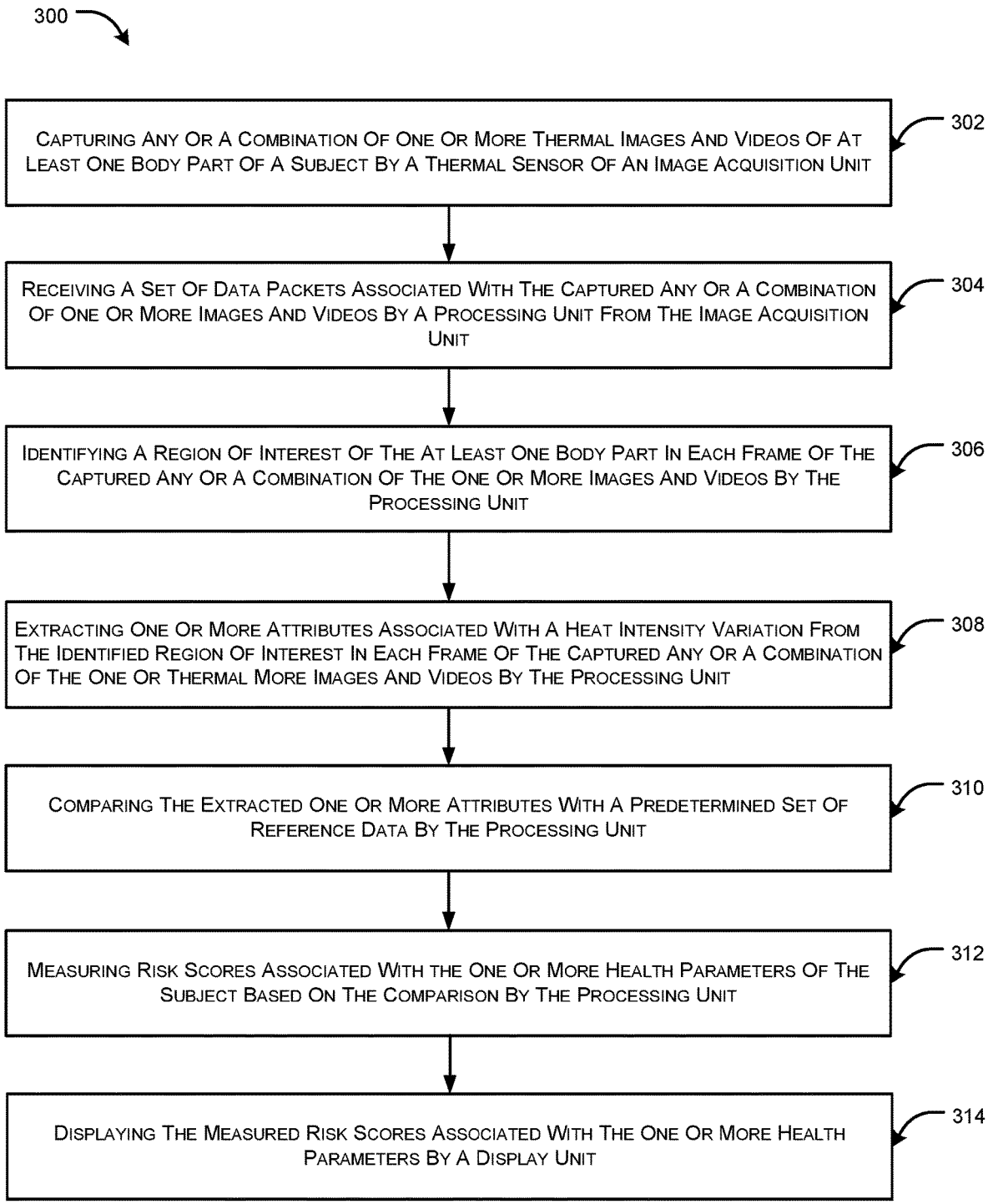
FIG. 3 illustrates a flow diagram illustrating a method for measuring health parameters of a subject, in accordance with an embodiment of the present disclosure.

FIG. 3 illustrates a flow diagram illustrating a method for measuring health parameters of a subject, in accordance with an embodiment of the present disclosure.

In an aspect, the proposed method may be described in the general context of computer-executable instructions. Generally, computer-executable instructions may include routines, programs, objects, components, data structures, procedures, modules, functions, etc., that perform particular functions or implement particular abstract data types. The method may also be practiced in a distributed computing environment where functions are performed by remote processing devices that are linked through a communications network. In a distributed computing environment, computer-executable instructions may be located in both local and remote computer storage media, including memory storage devices.

The order in which the method as described is not intended to be construed as a limitation and any number of the described method blocks may be combined in any order to implement the method or alternate methods. Additionally, individual blocks may be deleted from the method without departing from the spirit and scope of the subject matter described herein. Furthermore, the method may be implemented in any suitable hardware, software, firmware, or combination thereof. However, for ease of explanation, in the embodiments described below, the method may be considered to be implemented in the above-described system.

In context to a flow diagram 300, a block 302 pertains to capturing any or a combination of one or more thermal images and videos of at least one body part of a subject by a thermal sensor of an image acquisition unit. The image acquisition unit may be configured with a set of glasses including at least one glass, such as a two way mirror.

Further, a block 304 pertains to receiving a set of data packets associated with the captured any or a combination of one or more images and videos by a processing unit from the image acquisition unit.

Further, a block 306 pertains to identifying a region of interest of the at least one body part in each frame of the captured any or a combination of the one or more images and videos by the processing unit.

Further, a block 308 pertains to extracting one or more attributes associated with a heat intensity variation from the identified region of interest in each frame of the captured any or a combination of the one or thermal more images and videos by the processing unit.

Further, a block 310 pertains to comparing the extracted one or more attributes with a predetermined set of reference data by the processing unit. The predetermined set of reference data may be stored in a database operatively coupled to the processing unit. The one or more attributes associated with the heat intensity variation may be extracted to determine a blood flow, an artery region, and frequency properties of the blood flow in the artery region in the identified region of interest Further, a block 312 pertains to measuring risk scores associated with one or the more health parameters of the subject based on the comparison by the processing unit. The one or more health parameters are selected from a group including metabolic rate, state of diabetes mellitus condition, state of hypertension, state of dyslipidemia, body temperature, heart rate, respiratory rate, and the like.

Further, a block 314 pertains to displaying the measured risk scores associated with the one or more health parameters by a display unit.

In an embodiment, the region of interest may be identified based on correlation of the captured any or a combination of one or more thermal images and videos with any or a combination of one or more optical images and videos captured by an optical camera of the image acquisition unit.

Thus, it will be appreciated by those of ordinary skill in the art that the diagrams, schematics, illustrations, and the like represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

ADVANTAGES OF THE PRESENT DISCLOSURE

The present disclosure provides a simple and efficient solution which may obviate the foregoing limitations of conventional devices.

The present disclosure provides an improved system and method for measuring and/or monitoring health parameters of an individual.

The present disclosure provides a common system that may collectively monitor various diseases like cardiovascular disease, cerebrovascular disease, diabetes, hypertension, thyroid monitoring, lipidemia etc. of a subject, such as humans.

The present disclosure provides a simple and cost-effective health parameters measurement system and method which uses techniques, which are, robust, accurate, efficient, cost-effective, and easy to implement.

We claim:

1. A system for measuring one or more health parameters of a subject, the system comprising:
a set of glasses comprising at least one glass, wherein the at least one glass of the set of glasses are selected from a group comprising transparent glasses, translucent glasses, partially transparent glasses, and two-way mirrors;
an image acquisition unit configured with the set of glasses, the image acquisition unit comprising a thermal sensor for capturing any or a combination of one or more thermal images and videos of at least one body part of the subject; and
a processing unit operatively coupled to the image acquisition unit, and comprising one or more processors coupled to a memory, the memory storing a set of instructions executable by the one or more processors to:
receive a set of data packets associated with the captured any or a combination of one or more thermal images and videos from the image acquisition unit;
identify a region of interest of the at least one body part in each frame of the captured any or a combination of the one or more thermal images and videos;
extract one or more attributes associated with a heat intensity variation from the identified region of interest region in each frame of the captured any or a combination of the one or more thermal images and videos;
compare the extracted one or more attributes with a predetermined set of reference data that are stored in a database operatively coupled to the processing unit; and
in response to the comparison, measure risk scores associated with one or more health parameters of the subject.

2. The system as claimed in claim 1, wherein the one or more health parameters are selected from a group comprising a metabolic rate, state of diabetes mellitus condition, state of hypertension; state of dyslipidemia, body temperature, heart rate, and respiratory rate.

3. The system as claimed in claim 1, wherein the system comprises a display unit configured with the at least one glass, and operatively coupled to the processing unit, wherein the display unit is configured to display measured risk scores associated with the one or more health parameters.

4. The system as claimed in claim 3, wherein the display unit comprises a user interface, and wherein the display unit is configured behind the at least one glass.

5. The system as claimed in claim 3, wherein the system comprises a transceiver operatively coupled to the processing unit, and the image acquisition unit, and the display unit.

6. The system as claimed in claim 1, wherein the one or more attributes associated with the heat intensity variation is extracted to determine a blood flow, an artery region, and frequency properties of the blood flow in the artery region in the identified region of interest.

7. The system as claimed in claim 1, wherein the thermal sensor is a thermal camera, the thermal sensor senses heat or infrared radiations emitted from the body part of the subject and renders images and videos representing a spatial intensity of radiation, and wherein the thermal sensor is configured to capture any or a combination of the one or more thermal images and videos when the at least one body part is oriented at a first predefined angle with respect to the thermal sensor.

8. The system as claimed in claim 1, wherein the subject is a human, and wherein the at least one body part of the subject is a face of the subject.

9. The system as claimed in claim 1, wherein the image acquisition unit comprises an optical camera to capture any or a combination of one or more optical images and videos of the at least one body part of the subject, the optical camera being configured for identification of the at least one body part of the subject, and wherein the optical camera is configured to capture any or a combination of the one or more optical images and videos when the at least one body part is oriented at a second predefined angle with respect to the optical camera.

10. The system as claimed in claim 9, wherein the processing unit is configured to correlate the captured any or a combination of one or more thermal images and videos with the captured any or a combination of one or more optical images and videos to identify the region of interest.

11. The system as claimed in claim 1, wherein the image acquisition unit comprises a scanner unit for scanning the at least one body part of the subject, and wherein scanner unit is configured for authentication, identification and determining an orientation of the at least one body part of the subject.

12. The system as claimed in claim 1, wherein at least a portion of the glass is coated with a black vinyl wrap such that the at least portion of the glass acts as a mirror.

13. The system as claimed in claim 1, wherein the thermal sensor is positioned behind the at least one of glass, and wherein the at least one glass comprises a slot to expose the thermal sensor.

14. The system as claimed in claim 13, wherein the system comprises a shutter for opening and closing of the slot.

15. The system as claimed in claim 1, wherein the system comprises a frame for holding the set of glasses.

16. A method for measuring one or more health parameters of a subject, the method comprising:
capturing; by a thermal sensor of an image acquisition unit configured with a set of glasses, any or a combination of one or more thermal images and videos of at least one body part of the subject, wherein the set of glasses comprises at least one glass, wherein the at least one glass of the set of glasses are selected from a group comprising transparent glasses, translucent glasses, partially transparent glasses, and two-way mirrors;
receiving, by a processing unit, a set of data packets associated with the captured any or a combination of one or more images and videos from the image acquisition unit;
identifying, by the processing unit, a region of interest of the at least one body part in each frame of the captured any or a combination of the one or more images and videos;
extracting; by the processing unit, one or more attributes associated with a heat intensity variation from the identified region of interest region in each frame of the captured any or a combination of the one or thermal more images and videos;

comparing, by the processing unit, the extracted one or more attributes with a predetermined set of reference data that are stored in a database operatively coupled to the processing unit; and measuring, by the processing unit, risk scores associated with the one or more health parameters of the subject based on the comparison; and displaying, by a display unit, the measured risk scores associated with the one or more health parameters.

* * * * *